Figure 1:
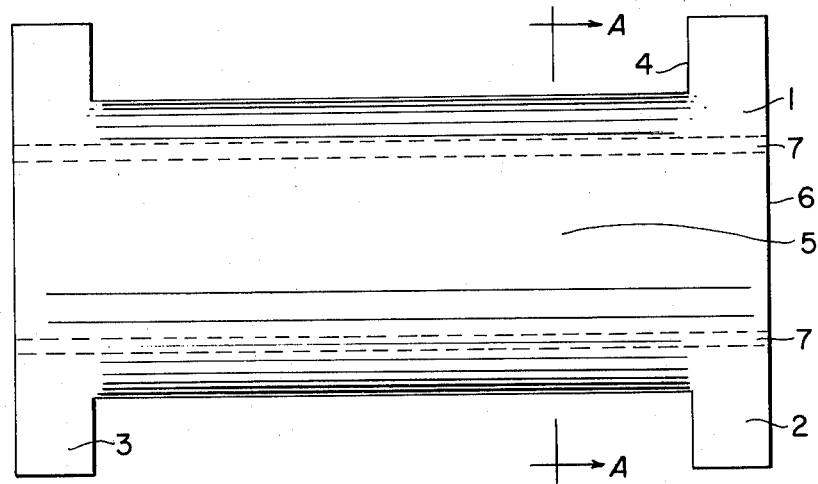

United States Patent [19]
Lapidot

[11] 3,976,081
[45] Aug. 24, 1976

[54] LAMINAR MIDDLE EAR VENT TUBE ASSEMBLY

[76] Inventor: Abraham Lapidot, 747 Montauk Highway, West Islip, N.Y. 11795

[22] Filed: Apr. 10, 1974

[21] Appl. No.: 459,603

[52] U.S. Cl............................................. 128/350 R
[51] Int. Cl.² ................... A61M 27/00; A61F 11/00
[58] Field of Search............ 003/DIG. 1; 128/349 R, 128/350 R

[56] References Cited
UNITED STATES PATENTS

| | | | |
|---|---|---|---|
| 3,434,869 | 3/1969 | Davidson | 128/349 R X |
| 3,453,194 | 7/1969 | Bennett et al. | 003/DIG. 1 |
| 3,530,860 | 9/1970 | Majoros | 128/350 R X |
| 3,585,647 | 6/1971 | Gajewski et al. | 128/334 R X |
| 3,673,612 | 7/1972 | Merrill | 128/349 R X |
| 3,688,317 | 9/1972 | Kurtz | 003/DIG. 1 |
| 3,807,409 | 4/1974 | Paparella et al. | 128/350 R |

Primary Examiner—Channing L. Pace

[57] ABSTRACT

A vent tube is disclosed which has improved resilient characteristics and heparinized poly-tetrafluoroethylene inner surface to prevent clotting of blood passing through it as it drains serious fluids and blood from middle ear to the exterior of the body. The substrate is comprised of a cross-linked polysiloxane resin of a molecular weight of at least 10,000 units. The inner lining of the laminar item is comprised of a layer coating of tetrafluoro polyethylene having a thickness of 2 to 10 mils and impregnated with an anticoagulant at or near its surface.

2 Claims, 2 Drawing Figures

LAMINAR MIDDLE EAR VENT TUBE ASSEMBLY

BACKGROUND OF THE INVENTION

At the present time there are available middle ear vent tubes of substantially the same shape as the claimed new and improved laminar vent device. One of these vent tubes is constructed entirely of elastomeric materials such as natural rubber or similar butadiene-styrene and the like. This device has the disadvantages that it is not possible to flex or compress the structure at the time that the otologist seeks to insert the vent into the small incision which he makes in the tissue membrane of the middle ear. The result of this is that the incision made must be substantially larger and slippage of the vent from the opening of the membrane is fairly common. In some cases it falls out of the ear and in some cases it goes within the inner ear itself causing much difficulty to the patient. The TEFLON flanges of the tube do not compress and deform against the surface of the membrane in which they have been implanted because the essential nature of this plastic material TEFLON is to slide along the surface of whatever it contacts and hence the efficiency of the flange shaped structure of this ear vent is dissipated because of the nature of the materials from which it is made.

On the other hand if one were to replace this grommet with a device made entirely of rubber or some similar elastomer which would deform and retain securely in the slit in the membrane wall a separate but equally serious problem would arise. This problem concerns the passage of fluids such as blood across and through the vent tube. Unless care is taken to insure a very smooth and inert surface within the tube where the channel of fluid flows a congestion and consequent plugging of the tube can and will occur. This plugging is frequently caused by tiny blood clot formation within the tube.

Therefore it can be seen that prior to the present invention the ear vents available each had problems of one type or another associated with their use. It remained for the present innovator to create a laminar ear vent tube which has none of these problems. The resultant discovery is the subject matter of this patent application more specifically detailed below:

OBJECTS OF THE INVENTION

It is a principal object of the invention to describe a unique ear vent tube which is laminar in its construction so as to have the concurrent properties of flexibility and surface resistance to fouling or congestion due to the formation of blood clots thereon.

It is a specific object of the invention to disclose a unique ear vent tube comprising a resinous main body portion which has flexure and a non-separable coating of a heparin treated TEFLON which will not permit blood clot formation in the tube when in contact with fluids moving through the tube.

THE INVENTION

Accordingly there has been provided a new laminar ear vent tube having an inner surface thereon of a chemically treated polytetrafluoro-ethylene film mounted on a base or substrate of a suitable elastomeric material particularly a silicone rubber which has a surface compatibility with skin tissue and membranes of the middle ear.

The device is therefore comprised of a grommet like or spool like tube about ¼ inch long and ⅛ inch in diameter having on either end a circumfertial flange. The body or base of the spool is comprised of (A) a substrate layer of from 30 to 50 mil thickness of an elastomeric resinous polysiloxane rubber in the shape of a flanged tube and (B) on the interior face of the said flanged tube there is superimposed and bonded thereto a layer of from 2 to 10 mil thickness of TEFLON having impregnated on its exterior surface from 0.01 to 0.10 mil thickness of a coating of a resin compatible anti-coagulant compound such as heparin.

The new ear vent tube has excellent flexure from its silicone rubber base and can thus be firmly implanted in the tissue slit in the tympanic membrane wall and because of its compressibility requires the surgeon to make less of an incision in the membrane when the vent tube is inserted.

Since the purpose of a middle ear vent tube implant is to create a means for constant drainage of fluids build up in the middle ear to the exterior it is imperative not only that the vent tube not slip out of place once it is implanted but also that the central bore or channel within the tube not become plugged or conjested with a buildup of any material. However in the condition which causes the need for an ear vent to arise there is also a blood release due to capillary rupture and hence some of the fluid issuing from the middle ear is blood which must pass over and through the vent tube on its course to the outer ear and discharge.

It is of course a fact that blood is prone to coagulation as it passes over a rough surface especially where it comes in contact with air. The blood in this case is made resistant to such clot formation by the presence of its heparin treated tublar interior face which in addition to being made of highly polished TEFLON to reduce surface friction has impregnated therein an anti-coagulant which slowly releases its content to the surface as it is contacted with blood and other fluids.

Figure 2:
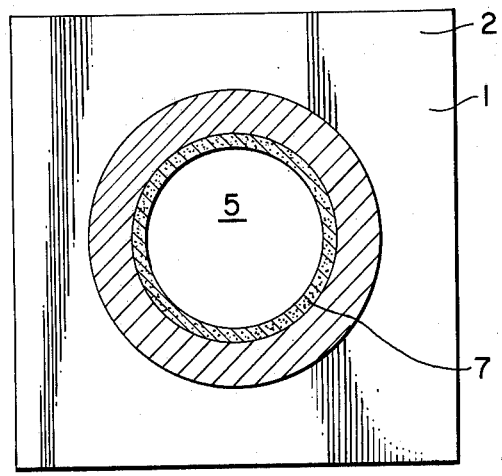

The invention can be further illustrated by reference to the accompanying figures in the attached drawing. FIG. 1 is a plan view of the device and FIG. 2 is a cross sectional view of the tube taken along the lines AA of FIG. 1.

Referring now to FIG. 1 of the drawing it can be seen that the vent tube comprises a substrate 1 which is molded silicon rubber preferably having a proximal flange 2 which rests inside the tympanic membrane and distal flange 3 which remains outside the membrane. There is an interior edge 4 on each flange which abuts against the membrane surface to hold the vent from passing in either direction entirely through the membrane. Within the substrate 1 lies channel 5 havng a tubular opening through which the fluid overflow passes from the middle ear to the outer ear. This channel is surrounded entirely by the interior layer 7 of heparin impregnated polytetrafluoroethylene. This structure is further illustrated by reference to the cross sectional view of FIG. 2. While it is noted that silicone rubber is the elastomeric material of choice for bonding to the TEFLON layer it must be noted also that other non toxic non irritating rubbers may also be used. The silicone rubber referred to is a polymeric substance formed by the heat treatment and cure of highly viscous le 10,1000 + units of silicone compositions such as dimethyl poly-siloxane or methyl phenyl polysiloxane. The silicone rubbers are siloxane polymers composed of a central chain of alternating silicone and oxygen atoms with alkyl groups attached to the silicone.

The silicone rubber base is bonded to the TEFLON layer without the need for an adhesive layer yet is can not be separtated therefrom by either chemical or physical means.

The laminate can be manufactured by starting with a silicone rubber 50 mil thick flanged tube which has been extrusion or injection molded. A solvent mixture of 45% ethanol, 20% methyl chloride, 10% dichlomethane, 10% acetone, 10% benzene and 5% acetic acid is aplied to the surface of this piece by immersion therein.

The same solvent or activator mixture is applied to a tube of TEFLON of 1.5 mm diameter and 3 mil wall thickness heparin impregnated TEFLON tube which TEFLON tube is inserted within the first silicone rubber tube to form a laminated flanged tube structure.

The laminar assembly was then placed in a mold or press and heated to about 240°F for about 5 minutes under 1000 psi pressure. The result was a firm structure which despite the heat treatment thereof was quite stable.

This piece was dipped for 10 seconds each into benyalkonium chloride and heparin solutions with the first primer coating being first dried before the second is applied.

I claim:
1. A laminar middle ear vent tube comprising:
   a. a substrate layer of from 30 to 50 mil thickness of an elastomeric resinous polysiloxane rubber in the shape of a flanged tube.
   b. on the interior face of said flanged tube substrate a bonded and superimposed layer of from 2 to 10 mil thickness of polytetrafluoroethylene having impregnated a coating of from 0.01 to 0.10 mil thickness of an anticoagulant compound.
2. A laminar ear vent tube according to claim 1 wherein the anticoagulant compound impregnated into the polytetrafluoroethylene surface layer is heparin.

* * * * *